United States Patent
Duda et al.

(10) Patent No.: US 9,757,419 B2
(45) Date of Patent: Sep. 12, 2017

(54) SKELETAL MUSCLE REGENERATION USING MESENCHYMAL SYSTEM CELLS

(75) Inventors: Georg Duda, Berlin (DE); Tobias Winkler, Berlin (DE); Georg Matziolis, Jena (DE); Philipp Von Roth, Berlin (DE); Carsten Perka, Berlin (DE)

(73) Assignee: Pluristem Ltd., Haifa (IL)

( * ) Notice: Subject to any disclaimer, the term of this patent is extended or adjusted under 35 U.S.C. 154(b) by 0 days.

(21) Appl. No.: 13/808,651

(22) PCT Filed: May 27, 2011

(86) PCT No.: PCT/EP2011/058730
§ 371 (c)(1),
(2), (4) Date: May 31, 2013

(87) PCT Pub. No.: WO2011/147967
PCT Pub. Date: Dec. 1, 2011

(65) Prior Publication Data
US 2013/0259843 A1    Oct. 3, 2013

Related U.S. Application Data

(60) Provisional application No. 61/348,870, filed on May 27, 2010.

(51) Int. Cl.
*A01N 63/00* (2006.01)
*A01N 65/00* (2009.01)
*A61K 35/28* (2015.01)
*C12N 5/0775* (2010.01)
*A61K 48/00* (2006.01)
*A61K 35/12* (2015.01)

(52) U.S. Cl.
CPC ............ *A61K 35/28* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61K 48/00* (2013.01); *A61K 2035/124* (2013.01)

(58) Field of Classification Search
CPC .. C12N 5/0663; C12N 5/0675; C12N 5/0662; C12N 5/0664; C12N 5/0665; C12N 5/0666; C12N 5/0668; C12N 5/0667; A61K 35/28
See application file for complete search history.

(56) References Cited

U.S. PATENT DOCUMENTS

| | | | |
|---|---|---|---|
| 6,911,201 B1 | 6/2005 | Merchav et al. |
| 7,534,609 B2 | 5/2009 | Merchav et al. |
| 7,678,573 B2 | 3/2010 | Merchav et al. |
| 8,524,496 B2 | 9/2013 | Meiron et al. |
| 8,529,888 B2 | 9/2013 | Meiron et al. |
| 9,096,827 B2 | 8/2015 | Meiron et al. |
| 2004/0258669 A1* | 12/2004 | Dzau et al. ................ 424/93.21 |
| 2005/0176143 A1 | 8/2005 | Merchav et al. |
| 2005/0181504 A1 | 8/2005 | Merchav et al. |
| 2008/0213227 A1* | 9/2008 | Aggarwal et al. ........... 424/93.7 |
| 2009/0004738 A1 | 1/2009 | Merchav et al. |
| 2010/0209403 A1 | 8/2010 | Meiron et al. |
| 2011/0129447 A1 | 6/2011 | Meretzki et al. |
| 2011/0129486 A1 | 6/2011 | Meiron |
| 2011/0171182 A1 | 7/2011 | Abelman |
| 2011/0256108 A1 | 10/2011 | Meiron et al. |
| 2011/0256159 A1 | 10/2011 | Meiron et al. |
| 2011/0256160 A1 | 10/2011 | Meiron et al. |
| 2011/0293583 A1 | 12/2011 | Aberman |
| 2012/0122220 A1 | 5/2012 | Merchav et al. |
| 2013/0004465 A1 | 1/2013 | Aberman |
| 2013/0039892 A1 | 2/2013 | Aberman |
| 2013/0323213 A1 | 12/2013 | Meiron et al. |
| 2013/0337558 A1 | 12/2013 | Meiron et al. |
| 2014/0017209 A1 | 1/2014 | Aberman et al. |
| 2014/0030805 A1 | 1/2014 | Kasuto et al. |
| 2014/0242039 A1 | 8/2014 | Meiron et al. |
| 2015/0125138 A1 | 5/2015 | Karnieli et al. |
| 2015/0216907 A1 | 8/2015 | Chajut et al. |
| 2015/0232797 A1 | 8/2015 | Kasuto et al. |

OTHER PUBLICATIONS

And Peault et al., 2007, Molecular therapy 15:867-877.*
De Bari et al., 2003, J. Cell. Biol. 160:909-918.*
Meng et al (20010 Jan., Neuromuscular Disorder 20:6-15.*
Kang et al., May 2010, Microvascular Research 80:310-316.*
Caplan et al 2009, J. Pathol. 217:318-324.*
Gayroud-Morel et al 2009, Regen. Med. 4:293-319.*
Dominici et al 2006, Cytotherapy 8:315-317.*
International Search Report, PCT/EP2011/058730, Aug. 9, 2011, European Patent Office, Rijswijk, NL.
Von Roth et al., "Immediate local transplantation of mesenchymal stem cells into a severely injured skeletal muscle in rats improves the functional outcome comparable to delayed transplantation," *Inflammation Research*, 59 (Supp.1): S42 (Mar. 2010) & 8th World Congress on Trauma, Shock, Inflammation, and Sepsis, Munich, DE Mar. 9-13, 2010.
Matziolis et al., "Autologous bone marrow-derived cells enhance muscle strength following skeletal muscle crush injury in rats," *Tissue Engineering*, 12(2): 361-67, (Feb. 2006).
Merritt et al., "Repair of Traumatic Skeletal Muscle Injury with Bone-Marrow-Derived Mesenchymal Stem Cells Seeded on Extracellular Matrix," *Tissue Engineering Part A*, 16(9): 2871-81, (Apr. 23, 2010).

(Continued)

*Primary Examiner* — Christopher M Babic
*Assistant Examiner* — Kelaginamane T Hiriyanna
(74) *Attorney, Agent, or Firm* — Wolf, Greenfield & Sacks, P.C.

(57) ABSTRACT

The present invention relates to a therapeutic substance and/or medicament and methods relating to the use of said substance and/or medicament for skeletal muscle regeneration using mesenchymal stem cells (MSCs) which can be applied directly or shortly after muscle damage or injury.

28 Claims, 5 Drawing Sheets

(56) References Cited

OTHER PUBLICATIONS

Winkler et al., "Dose-Response Relationship of Mesenchymal Stem Cell Transplantation and Functional Regeneration After Severe Skeletal Muscle Injury in Rats," *Tissue Engineering Part A*, 15(3): 487-92 (Mar. 2009).
Winkler et al., "In vivo visualization of locally transplanted mesenchymal stem cells in the severely injured muscle in rats," *Tissue Engineering Part A*, 14(7): 1149-60 (Jul. 2008).
U.S. Appl. No. 14/432,402, filed Mar. 30, 2015, Ofir et al.
U.S. Appl. No. 14/835,124, filed Aug. 25, 2015, Aberman.

* cited by examiner

Fig. 1

Course of physiological regeneration

Fig. 2

7 Tesla MRI
1 week after trauma

Fig. 3

Fast twitch

SKELETAL MUSCLE REGENERATION USING MESENCHYMAL SYSTEM CELLS

This application is a national stage application of PCT/EP2011/058730, filed May 27, 2011, which claims priority to U.S. Provisional Patent Application No. 61/348,870, filed May 27, 2010, each of which is incorporated by reference herein in their entirety.

The present invention relates to a therapeutic substance and/or medicament and methods relating to the use of said substance and/or medicament for skeletal muscle regeneration using mesenchymal stem cells (MSCs) which can be applied directly or shortly after muscle damage or injury.

BACKGROUND OF THE INVENTION

Skeletal muscle trauma often leads to severe functional deficits due to insufficient regeneration of the musculature. Approaches to reduce the collateral damage due to soft tissue trauma have until recently been predominantly conservative and based on preparing the muscular macrostructure to enable intrinsic healing mechanisms of the muscle. Such approaches include the traditional RICE approach (Rest Ice Compression Elevation) and the suturing of retracted muscle stumps, which allow the intrinsic regenerative capacities of the muscle to take effect. The central process of such intrinsic mechanisms is represented by the activation of satellite cells and their contribution to new myofibers (Mauro, A., J Biophys Biochem Cytol 9, 493, 1961).

A relatively recent concept in muscle and tissue regeneration is based on the idea of introducing progenitor cells or other cells capable of inducing or undergoing regeneration at the site of muscle or tissue injury. Cells with regenerative potential have been proposed to be able to stimulate the growth and healing process of human tissues. Mechanisms of this stimulation are on the one hand a secretion of trophic factors and of immunomodulatory factors and on the other hand a contribution to contractile muscle fibers by the progenitor cells.

Mesenchymal stem cell (MSC) therapy offers an effective tool in the regeneration of muscle function after severe trauma. MSCs are mesenchymal cells found, e.g. in bone marrow, dermis, placenta, adipose tissue and periosteum. A part of these cells are capable of differentiating into specific types of mesenchymal or connective tissues including adipose, osseous, cartilaginous, muscular tissue and elastic and fibrous connective tissues.

MSCs exhibit a high proliferation potential and lower donor site morbidity when compared to muscle-derived cells, thus rendering them an ideal candidate for clinical application in muscle regeneration.

New therapeutic possibilities have recently been proposed for muscle regeneration that are based on the idea of an extrinsic support of the cellular regeneration by increasing the number of progenitor cells in the injured tissue. Initial experiments showed that the transplantation of myoblasts could partially restore dystrophin in myofibers of musculature deficient of this protein (Partridge, T. A., et al. Nature 337, 176, 1989, Huard, J., et al. Clin Sci (Lond) 81, 287, 1991) and improve the condition of regenerating denervated and ischemic musculature compared to undamaged control muscles (DeRosimo, J. F., et al. Cell Transplant 9, 369, 2000, Arcila, M. E., et al. J Neurobiol 33, 185, 1997).

The clinical application of MSCs in skeletal muscle regeneration in the prior art is limited. To date, few experimental studies have investigated the effect of local MSC transfer on skeletal muscle regeneration, two of which evaluated the functional outcome of cellular therapy (Matziolis, G., et al. Tissue Eng 12, 361, 2006, Natsu, K., et al. Tissue Eng 10, 1093, 2004).

Previous studies have investigated the effect of MSCs in treating toxin-damaged muscle tissue. For example, genetically modified human mesenchymal stem cells were injected in dystrophin deficient musculature of immunosuppressed mice after toxic damage. No improvement in muscle contraction forces could be found and the authors stated that MSCs were in fact currently unsuitable for the treatment of muscle dystrophies (Gang et al. Experimental Cell Research 315: 2624, 2009). Alternative cell types have also been investigated in treating skeletal muscle injury. The transplantation of human umbilical cord blood cells into crushed gastrocnemius muscles demonstrated little change in muscle regeneration, whereby no functional effect in muscle regeneration was shown (Brzoska et al, Experimental Hematology, 2006).

The applicant has previously demonstrated that the local transplantation of $1 \times 10^6$ autologous MSCs one week after an injury to the soleus muscle could improve muscle forces measured three weeks after application (Matziolis, G., et al. Tissue Eng 12, 361, 2006). The functional effect of the MSCs increases with the transplanted cell number. The one week delay between injury to the soleus muscle and local injection of MSCs adhered to the commonly accepted paradigm that the initial inflammatory phase, with a high activity of macrophages, would be disadvantageous for the putative integration and regenerative effect of the applied MSCs (Jarvinen, M. and Sorvari, T. Acta Pathol Microbiol Scand [A] 83, 259, 1975, Li, Y. and Huard, J. Am J Pathol 161, 895, 2002).

The biological processes which are triggered and maintained by an injury to skeletal muscle tissue are diverse. The natural course following a skeletal muscle injury is initiated by an inflammatory phase, which is determined by the invasion of neutrophils and later macrophages (see FIG. 1, adapted from Li, Y. and Huard, J. Differentiation of muscle-derived cells into myofibroblasts in injured skeletal muscle, Am J Pathol 161, 895, 2002). The presence of inflammatory cells within the tissue starts immediately after injury and lasts up to several weeks. Their initial task is to remove necrotic tissue to enable regenerative processes, which begin with the activation of satellite cells already from the third day after muscle fiber damage.

The prior art which relates to mechanisms of muscular regeneration by stem cells is particularly focused on the paracrine regeneration stimulating or immunomodulatory effect of the transplanted cells, on the impact of fusion of the cells with myofibers or a differentiation into myocytes. The first most likely improves the survival of myocytes within the target tissue and on the other hand might also decrease the collateral damage, which is effected by local inflammation.

Compared to the immediate injection, MSCs that are locally transplanted seven days after injury are confronted with some inflammation in the muscle tissue, but to a significantly lower extent. At this time regenerating myofibers are predominant, although collagenous fibrous tissue has already been deposited in defect zones and in the interstitium.

The ideal time to transplant progenitor cells for the regeneration of skeletal muscle damage has not been established. To our knowledge, previous work on skeletal muscular regeneration has provided no recommendation regarding application time point due to the lack of studies aimed at this question. Previous reports, describing the transplantation of human umbilical cord blood cells into crushed gastrocnemius muscles of immunosuppressed mice or the transplantation of myoblasts into dystrophin deficient muscles after toxin injury could not demonstrate any therapeutic effect leading to the assumption that the immediate transplantation of progenitor cells is prone to a worse outcome because of the initial hostile microenvironment (Gang et al. Experimental Cell Research 315: 2624, 2009; Rousseau al. Cell Transplant. 19(5), 589, 2010).

The general view found in the prior art is that MSCs transplanted directly after muscle trauma would not be able to exert their effect on regeneration because of the hostile microenvironment. The astonishing aspect of the present invention is that an immediate application of MSCs after a muscle injury is equivalently capable of increasing muscle contraction forces as a delayed transplantation. The present invention provides a more efficient and more amenable alternative method for the local transplantation of MSCs, characterized in that the MSCs are applied immediately or shortly after skeletal muscle injury. The prior art method of transplantation one week after injury presents multiple disadvantages regarding patient discomfort and risk. The unexpected effect that muscle regeneration is effective after immediate MSC transplantation is of enormous pragmatic importance as the transplantation of MSCs directly after muscle trauma reflects current clinical demands.

SUMMARY OF THE INVENTION

In light of the prior art the technical problem underlying the present invention is to provide a therapeutic substance and/or medicament and methods relating to the use of said substance and/or medicament for skeletal muscle regeneration using mesenchymal stem cells (MSCs) which can be applied directly or shortly after muscle damage or injury.

This problem is solved by the features of the independent claims. Preferred embodiments of the present invention are provided by the dependent claims.

Therefore, the invention relates to mesenchymal stem cells for use as a medicament for the treatment of skeletal muscle damage or injury within 72 hours, preferably within 48 hours, more preferably within 24 hours or more preferably within 12 hours, after muscle damage or injury.

The invention relates in a preferred embodiment to mesenchymal stem cells for use as a medicament for enhancing the functional recovery and/or structural regeneration of skeletal muscle damage or injury, preferably in addition to reducing pain associated with said muscle injury in a subject, whereby treatment with said MSCs occurs within 72 hours, preferably within 48 hours, more preferably within 24 hours or more preferably within 12 hours, after muscle damage or injury.

In one embodiment the mesenchymal stem cells of the present invention are characterized in that the MSCs are autologous MSCs.

In one embodiment the mesenchymal stem cells of the present invention are characterized in that the MSCs are allogeneic MSCs.

In a preferred embodiment the mesenchymal stem cells of the present invention are characterized in that the MSCs are bone marrow MSCs, preferably extracted from bone marrow.

In one embodiment the mesenchymal stem cells of the present invention are characterized in that autologous MSCs are obtained from the patient intraoperatively during the same operation in which the MSCs are to be administered.

In one embodiment the mesenchymal stem cells of the present invention are characterized in that the MSCs are concentrated by the depletion of red blood cells from a bone marrow aspiration, preferably using the Harvest SmartPReP 2 system, and prepared as the nuclear cell fraction of the bone marrow sample.

In one embodiment the mesenchymal stem cells of the present invention are characterized in that the MSCs are obtained from a patient before elective surgery and prepared and/or expanded using in vitro cell culture.

In a preferred embodiment the mesenchymal stem cells of the present invention are intended for use as a medicament for the treatment of skeletal muscle damage or injury 1, 2, 3, 4, 5, 6, 7, 8, 9, 10, 11 or 12 hours after said injury, or 14, 16, 18, 20 or 22 hours after said injury In one embodiment the mesenchymal stem cells of the present invention are characterized in that the skeletal muscle injury to be treated is an injury incurred during hip replacement, during surgery of the spine, a muscle injury incurred in association with rotator cuff injuries and/or traumatic soft tissue injuries with concomitant skeletal muscle injuries.

In one embodiment the mesenchymal stem cells of the present invention are characterized in that the MSCs are selected and isolated using plastic adherence, FACS and/or MACS cell separation.

In a preferred embodiment the mesenchymal stem cells of the present invention are characterized by $CD44^+$, $CD73^+$, $CD90^+$ and/or $CD45^-$ markers.

In a preferred embodiment the mesenchymal stem cells of the present invention are characterized in that
   CD105 CD73 and/or CD90 markers are positive ($\geq 95\%$), and
   CD45, CD34, CD14 or CD11b, CD79a or CD19, and/or HLA-DR markers are negative ($\leq 2\%$).

The markers provided herein for the MSCs of the present invention can be used in combination with one another, or individually as required.

In a preferred embodiment the mesenchymal stem cells of the present invention are characterized in that the muscle damage or injury to be treated is selected from the group comprising direct trauma, laceration, abrasion, bruising, crush injury, contusion injury by short or long impact, tear, strain and/or sprain preferably selected from the group comprising contusion injury of short or long impact, crush injury, laceration, strain, and more preferably selected from the group comprising muscle laceration, muscle injury incurred by cutting or dissection of, or surgical incision into, skeletal muscle, such as muscle injuries that occur during operative or surgical intervention, also known as myotomy, sport injuries, such as torn muscles or torn muscle fibres, and/or injuries occurring from stretching or overstretching muscles and/or injuries incurred during surgery or operation around the spinal cord and/or vertebral column, in addition to rotator cuff ruptures.

In one embodiment the mesenchymal stem cells of the present invention are characterized in that the MSCs are to be administered locally to injured muscle and/or to the healthy tissue surrounding the damaged musculature, preferably within 0.5 mm to 100 mm, preferably between 0.5 mm to 50 mm or more preferably within 0.5 mm to 20 mm of the muscle damage.

In one embodiment the mesenchymal stem cells of the present invention are characterized in that the MSCs are to be administered via injection.

In one embodiment the mesenchymal stem cells of the present invention are characterized in that the MSCs are to be administered in the arterial blood vessels leading to the site of muscle damage.

In one embodiment the mesenchymal stem cells of the present invention are characterized in that the therapeutically effective amount of MSCs to be administered is between $1\times10^4$ and $1\times10^{10}$ MSCs/kg body weight.

In one embodiment the mesenchymal stem cells of the present invention are characterized in that the MSCs are present in a pharmaceutical composition comprising a therapeutically effective amount of MSCs in addition to at least one pharmaceutically acceptable substance.

In one embodiment the mesenchymal stem cells of the present invention are characterized in that the MSCs are genetically modified, for example to produce and secrete proteins, such as IGF-1, that influence the regeneration or inflammatory process; for example to produce and secrete proteins that inhibit processes impairing regeneration, such as TGF-beta inhibiting fibrosis.

In one embodiment the mesenchymal stem cells of the present invention are characterized in that the MSCs have been linked or coupled to proteins or other substances in vitro in order to influence the regeneration or inflammatory process.

The invention further relates to the use of mesenchymal stem cells as a medicament, and/or for the preparation of a medicament, for the treatment of skeletal muscle damage or injury within 72 hours, preferably within 48 hours, more preferably within 24 hours or more preferably within 12 hours, after muscle damage or injury.

The invention further relates to a method for treating skeletal muscle damage or injury in animals or humans, characterized by administering a therapeutically effective amount of mesenchymal stem cells (MSCs) to the mammal within 72 hours, preferably within 48 hours, more preferably within 24 hours or more preferably within 12 hours, for example immediately or shortly after muscle damage or injury.

In a preferred embodiment the method of the present invention is characterized in that the MSCs are autologous MSCs. In a further embodiment the method of the present invention is characterized in that the MSCs are allogeneic MSCs. The source of the MSCs can be either from the same donor as to whom the cells are administered (autologous) or from a different donor (allogeneic). MSCs sourced from a different donor can be administered in combination with other active substances, such as immunomodulators, wherever necessary to facilitate treatment of a patient with allogeneic cells.

The present invention encompasses MSCs that are preferably extracted from bone marrow. Alternatively, the present invention also encompasses the application of MSCs that are extracted from blood, either by concentration by centrifugation or other concentration procedures or by selection procedures, e.g. positive or negative cell sorting, or by isolation procedures and culturing and/or proliferation of the cells. The present invention encompasses the application of MSCs that are extracted from adipose tissue, e.g. obtained from liposuction procedures. The present invention encompasses the application of MSCs that are extracted from the placenta, by digesting placental tissue and culturing and proliferation of mesenchymal-like cells. The present invention also encompasses the application of MSCs that are extracted from parenchymal organs by digestion and culturing and proliferation of mesenchymal cells. The present invention also encompasses the application of MSCs that are extracted from muscle tissue, e.g. by biopsies or by excision of muscle tissue. The present invention also encompasses the application of MSCs that are extracted from periosteum. The present invention also encompasses the application of MSCs that are extracted from skin.

In a further embodiment the method of the present invention is characterized in that autologous MSCs are extracted from the patient intraoperatively during the same operation in which the MSCs are administered. This allows treatment of patients from accidents or emergencies to also benefit from the technology of the present invention. Cells are extracted during operative procedures, purified or sorted to varying extents, depending on the particular patient and application, and administered immediately. This represents the meeting of current and future clinical demands, avoiding the need for pre-extracted MSCs and in vitro culturing before application.

In a preferred embodiment the method of the present invention is characterized in that the MSCs are concentrated by the depletion of red blood cells from a bone marrow aspiration, preferably using the Harvest SmartPReP 2 system, and administered as the nuclear cell fraction of the bone marrow sample. The Harvest SmartPReP systems, Sepax systems or other systems that are suited for the separation of nuclear cell fractions from bone marrow aspirations, which contain the MSCs to be administered, are also encompassed by the present invention. Such separation or concentration systems allow the intraoperative administration of MSCs. The nuclear fraction of the bone marrow sample can then be directly administered, or further cell separations can be undertaken before administration, if the patient or application demands a higher purity of MSCs.

In a further embodiment the method of the present invention is characterized in that the MSCs are extracted from a patient before elective surgery and prepared and/or expanded using in vitro cell culture. In a further embodiment the method of the present invention is characterized in that the MSCs are applied in the treatment of muscle injury after hip replacement, skeletal muscle damage during surgery of the spine, muscle injury incurred in association with rotator cuff injuries and/or traumatic soft tissue injuries with concomitant skeletal muscle injuries.

In a preferred embodiment the method of the present invention is characterized in that the MSCs are selected and isolated using plastic adherence, FACS and/or MACS cell separation. In a further embodiment the method according to the invention is characterized in that the FACS and/or MACS separation is carried out using $CD44^+$, $CD73^+$, $CD90^+$ and/or $CD45^-$ markers, and/or the following criteria, characterized in that CD105 CD73 and/or CD90 markers are positive ($\geq 95\%$) and CD45, CD34, CD14 or CD11b, CD79a or CD19, and/or HLA-DR markers are negative ($\leq 2\%$). These criteria for MSC characterization have been established by the International Stem Cell Society.

FACS (Fluorescence-activated cell sorting) is a method of cell separation based on flow cytometry well known to practitioners in the art. MACS (Magnetic activated cell sorting) relates to a further cell separation technique based on separation of cells depending on their extracellular antigens and is also known to one skilled in the art.

In a preferred embodiment the method of the present invention is characterized in that the muscle damage or injury to be treated is selected from the group comprising direct trauma, laceration, abrasion, bruising, crush injury, contusion injury by short or long impact, tear, strain and/or sprain, preferably selected from the group comprising contusion injury of short or long impact, crush injury, laceration, strain, and more preferably selected from the group comprising muscle laceration, cutting or dissection of, or surgical incision into, skeletal muscle, such as muscle injuries that occur during operative or surgical intervention, also known as myotomy. Further preferred skeletal muscle injuries to be treated in the method and with the products of the present invention are sport injuries, such as torn muscles or torn muscle fibres, and/or injuries occurring from stretching or overstretching muscles. Further injuries to be treated relate to muscle injuries incurred during surgery or operation around the spinal cord and/or vertebral column, and to rotator cuff ruptures.

The application of MSCs according to the present invention also relates to their use in pain therapy, whereby the MSCs applied in enhancing skeletal muscle regeneration additionally provide a pain-relieving effect. The application of MSCs leads to reduced pain in the subject treated with the MSCs as opposed to subjects not treated with the MSCs.

The application of MSCs according to the present invention also relates to their ability to accelerate the rehabilitation time after skeletal muscle injury, to improve contraction forces of the treated muscles, to reduce scar generation and scar size of postoperative wounds above muscles treated with MSC-therapy. Further, concerning the treatment of approach related skeletal muscle injuries by MSC transplantation, e.g. during or after hip arthoplasty, the present invention also relates to the ability of MSCs to reduce intramuscular scar formation, to improve the range of motion of the joint, to decrease the frequency of limping, to reduce the frequency of periarticular ossifications and consecutively to prolong the time to loosening of prostheses, e.g. hip prostheses.

The present invention therefore provides significant improvements in skeletal muscle regeneration in more than one sense, because wound healing is enhanced, functional regeneration is enhanced and pain surrounding the wound and also systematically is reduced in patients having received the MSCs. This unique combination of features has not been disclosed in the prior art, whereby each of the effects alone, in combination with one other of the effects, or all three effects in combination, may occur. When arising in combination, the effects as described herein interact with one another in synergy to provide a unique outcome in regards to healing, structural and functional regeneration and/or restoration of skeletal muscle after injury.

In a further embodiment the method of the present invention is characterized in that the MSCs are applied locally to injured muscle and/or to the healthy tissue surrounding the damaged musculature, preferably within 0.5 mm to 100 mm, preferably between 0.5 mm to 50 mm or more preferably within 0.5 mm to 20 mm of the muscle damage.

In a preferred embodiment the method of the present invention is characterized in that the MSCs are administered via injection. In a further embodiment the method of the present invention is characterized in that the MSCs are applied in the arterial blood vessels leading to the site of muscle damage.

In a preferred embodiment the method of the present invention is characterized in that the therapeutically effective amount of MSCs to be administered is between $1 \times 10^4$ and $1 \times 10^{10}$ MSCs/kg body weight.

In a further preferred embodiment the method of the present invention is characterized in that the MSCs are administered as a pharmaceutical composition comprising a therapeutically effective amount of MSCs in addition to at least one pharmaceutically acceptable substance.

DETAILED DESCRIPTION OF THE INVENTION

One of the major problems in the implantation of total hip replacements via the classical transgluteal approach is associated injury of the gluteus medius muscle. This results in a consecutive loss of muscle tissue and subsequent replacement with scar tissue. This leads directly to a functional deficit of the stabilising musculature of the pelvis and pronounced patient limping of varying strengths. Over long periods of time this also leads to bone resorption or degeneration at the femoral insertion site of the injured muscle around the proximal prosthesis stem. Because loosening or dislocation of prostheses occur more often in cases where the pelvitrochanteric musculature is of limited coordination and stabilisation, a negative effect on the life of the hip replacement can be expected.

Furthermore, newly established minimally invasive methods often lead to a pronounced indirect traumatisation of the musculature surrounding the hip in the sense of a pressure or crush trauma and denervation trauma due to surgical entry. Such injury and muscle trauma leave no expectation of a fundamental improvement of the hip or pelvis musculature function.

At the present time there exists no established therapy for the regeneration of injured musculature.

Muscle injuries can occur via many different mechanisms. Possible injury types are direct trauma, such as cuts and abrasions, bruises or contusions, tears, strains or sprains from indirect trauma, ischemia and neurological dysfunctions. In the fields of orthopaedic and emergency surgery, cut and contusion traumas play a critical role.

Various phases of muscle regeneration are described that take place throughout the process of healing.

(1) Degeneration and Inflammation phase: In the first few days after trauma, portions of muscle fibres die and an inflammatory reaction occurs. The necrotic area becomes infiltrated by mono-nuclear cells, activated macrophages and T-cells. The activated lymphocytes secrete a large number of various messenger substances which subsequently trigger an inflammatory response. The regeneration process is then initiated, but is initially inhibited by the formation of an intra- and extra-muscular haematoma. In addition, the haematoma also promotes the formation of unwanted scar tissue.

(2) Reparation phase: In the following 7-10 days the necrotic muscle fibre portions are cleared away by macrophages and regeneration of the muscle begins. The satellite cells migrate into the damaged muscle fibres or form into new fibres. Capillaries also immigrate into the regenerating area. The regeneration process reaches its most active point at approximately 14 days after trauma.

(3) Restoration phase (fibrosis): This phase occurs in cross-over with the previous phase and can last as long as four weeks. A normal fibre diameter and the complete differentiation of fibre types is achieved through a re-innervation of the regenerating tissue.

In light of this knowledge, experimental animal studies were typically carried out involving the transplantation of cells one week after muscle trauma. The concept underlying delayed transplantation was based on sound scientific rational. The cellular and tissue environment of immediately post-trauma muscle clearly indicated a negative effect on transplanted cells.

Considering that the transplantation alone represents a significant stress for both transplanted cells and the receiving tissue, the combination of this stress in an immediate post-trauma tissue environment was overwhelmingly likely to have a negative impact on any potential additive regeneration effect. Therefore the transplantation of cells in a regeneration stimulatory environment (phase 2) offered the highest chances of success. As a result of this the clinical application and usefulness of stem cell transplantation, as known in the prior art, has been demonstrated on the basis of this delayed transplantation concept.

Despite this, a delayed transplantation strategy does not represent an ideal procedure for everyday clinical procedure. Muscles can be iatrogenically injured during an operation or during an accident-related trauma. In both situations, an ideal solution is to provide MSCs at the same time as the operation or trauma in order to avoid a further treatment of the patient one week after the operation or accident. Every patient intervention carries potential risks, such as infection or incidents of narcosis. Therefore the application of MSCs should be carried out at the same time as the initial treatment whenever possible. Even in the case of a potential reduced muscle regeneration effect due to early MSC application, the related risk reduction to the patient due to the minimalisation of medical procedures represents a significant advantage.

The present invention therefore represents an alternative to delayed MSC transplantation therapy, which overcomes the disadvantages of the prior art.

Therefore, the invention provides a method for treating skeletal muscle damage or injury in animals or humans, characterized by administering a therapeutically effective amount of mesenchymal stem cells (MSCs) to the mammal immediately, shortly or up to 72 hours after injury.

It is important to note that the method described herein relates to a method for functional regeneration of skeletal muscle. The described application or use of MSCs enhances muscle recovery, so that the wound or injury exhibits enhanced healing in addition to enhanced functional contractile properties, as described in the examples below. The improvement in fast twitch and tetanic forces demonstrated in muscle treated according to the present invention has not been shown before. Various studies in the prior art have attempted to analyse the fate of transplanted cells, although it remained unclear whether functional benefits were achieved via transplantation of MSCs after skeletal muscle injury.

A further aspect is that MSCs are able to down-regulate the inflammatory immune response. It has been shown in the prior art that MSCs influence the secretion of several pro-inflammatory cytokines and inhibit the formation of dendritic cells from monocytes. These effects have been made use of in clinical studies against graft-versus-host disease, where MSCs have been systemically administered and were successful in mitigating the reaction. Thus, it is the MSCs own properties that enable them to alter the intramuscular inflammation. Further addressed mechanisms of MSC therapy include the transfer of superficial and other proteins from transplanted cells to host cells. E.g. it could be shown that MSCs are able to transfer human leukocyte antigens to other cells.

In a recent study the inventor labeled MSCs with iron oxide nanoparticles and followed them in vivo via magnetic resonance imaging one week after transplantation into the injured soleus muscle. Transplanted cells could be detected in a circumscribed area over a period of three weeks. Migration of MSCs within the muscle did not take place. A possible explanation for such findings was that the non-existent migration was to be found due to the natural barrier of fibrosis, which the cells encounter at this time. Surprisingly, when MSCs are transplanted immediately after injury this barrier to cellular migration is not present, as cross-linking of the extracellular matrix starts hours to days later. The intramuscular haematoma spreads throughout the muscle, creating optimal preconditions for the distribution of immediately transplanted cells. The surprising effect, that the immediately transplanted cells of the present invention function equally well in muscle regeneration as those in delayed transplantation, despite the increased degeneration and inflammation that is present shortly after injury, is enhanced by the unexpected fact that cell migration is favored early after muscle injury.

It is therefore particularly advantageous, in one embodiment of the present invention, that the MSCs are administered by local application to injured muscle and/or to the healthy tissue surrounding the damaged musculature, preferably within 0.5 mm to 100 mm, preferably between 0.5 mm to 50 mm or more preferably within 0.5 mm to 20 mm of the muscle damage. Also encompassed within the invention is the administration of cells 0.5, 1, 2, 3, 4, 5, 6, 7, 8, 9, 10, 12, 15, 20, 25, 30, 35, 40, 45, 50, 60, 70, 80, and/or 90 mm from the muscle injury. Administration of MSCs within these specific regions surrounding the muscle injury functions in synergistic combination with the surprising effect of enhanced cell migration, which is present immediately after injury, to facilitate the regenerative effect of the transplanted MSCs. Administration of cells within these particular ranges at the time points as described within the present application assists with the surprising effect that wound healing and functional muscle regeneration is enhanced beyond what would have been expected. These administration sites provide significant improvements in cell migration in comparison to administration at other sites or via other methods.

The present invention relates to the immediate or prompt application of MSCs in the treatment of skeletal muscle damage. The phrase relating to application of MSCs "within 72 hours after muscle damage or injury" refers to the administration of MSCs to the patient immediately, for example within one minute or after a few minutes, up until 72 hours after injury. The invention relates to a preferred application of MSCs shortly after the injury, in comparison to the application of MSCs one week after injury in the prior art. Therefore the application of MSCs after 72 hours still represents a significant improvement over the prior art method of application one week post-injury. In a further preferred embodiment the MSCs are applied within 48 hours after injury, or more preferably within 24 hours after injury. In further preferred embodiments the MSCs are applied after 1, 2, 3, 4, 5, 6, 7, 8, 9, 10, 11 or 12 hours after injury, or 14, 16, 18, 20 or 22 hours after injury. An immediate or prompt application is preferred, such as within the first hour after injury, although, because many patients remain in medical care, for example in hospitals, for some time after injury the administration of MSCs up to a few days after injury still represents a significant improvement over the prior method of application after one week, which requires a separate visit and treatment of the patient by relevant medical professionals.

The term "skeletal muscle" refers to striated muscle tissue under control of the somatic nervous system. It encompasses all muscle types outside of cardiac and smooth muscle.

As used herein the term "pharmaceutical composition" means a composition comprising a mesenchymal stem cell preparation and at least one ingredient that is not an active ingredient whereby the composition can be safely and effectively used as a product to obtain or achieve a desired outcome. The term "pharmaceutical composition" as used herein means compositions which result from the combination of individual components which are themselves pharmaceutically acceptable. For example, where intravenous administration is foreseen, the components are suitable or acceptable (in both quality and quantity) for intravenous administration. The subject of the MSC administration according to the present invention is a mammal. The mesenchymal stem cells of the present invention can be administered to mammals, preferably humans or livestock, by numerous routes, such as intravenously, intraarterially or intramuscularly. The dose administered may be between about $10^3$ and about $10^{11}$ cells per dose, preferably between $1\times10^4$ and $1\times10^{10}$ MSCs/kg body weight or between $1\times10^4$ and $1\times10^9$ MSCs/kg body weight, or other amounts understood by a person of ordinary skill in the art to be therapeutically effective as a therapy to enhance muscle regeneration.

The disclosure presented herein is directed towards a pharmaceutical composition which can be administered through a variety of routes including intravenously, intraarterially, intramuscularly or directly into or onto the affected individual. When the medicament is delivered via an injection, the injection of the mesenchymal stem cell composition can occur as a single injection or multiple injections at any location inside or outside the body. The dose is administered to a subject wherein the amount of the mesenchymal stem cell preparation delivered to the subject from the medicament is about that which is therapeutically effective for treating damage of the skeletal musculature. Additionally, the medicament may optionally include additional components such as salts, stabilizers and antimicrobials without departing from the spirit and scope of the claimed invention. The medicament of the present invention contains a mesenchymal stem cell preparation and a pharmaceutically acceptable carrier. The quantity and nature of the mesenchymal stem cells to be incorporated in the composition will vary depending on desired therapeutic effect and the time span for which the composition is to provide a therapeutic effect. The quantity of mesenchymal stem cells in the medicament is that which will deliver a therapeutically effective amount for treating damage of skeletal musculature. Of course, the concentration and character of the mesenchymal stem cells to be included in the medicament will vary depending upon the components used in the composition, the route by which it is administered, the symptoms and details of the muscle damage which requires treatment as well as other factors known to those of skill in the art.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

DESCRIPTION OF THE FIGURES

The invention is further described by the figures. These are not intended to limit the scope of the invention.

DETAILED DESCRIPTION OF THE FIGURES

Figure 1:
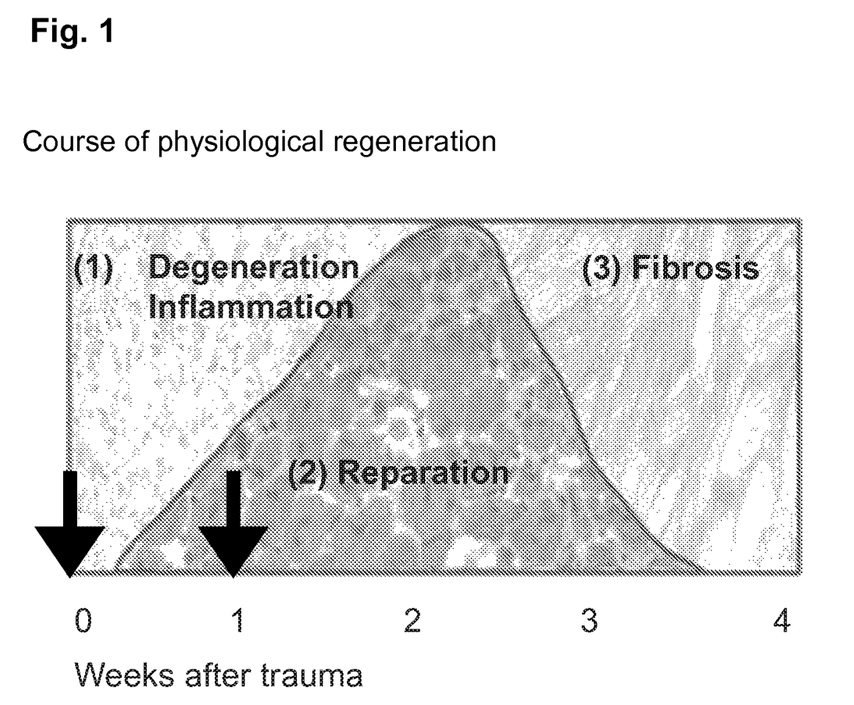
FIG. 1: A schematic representation of the course of physiological regeneration after skeletal muscle injury.

FIG. 1: Course of physiological regeneration. The natural course following a skeletal muscle injury as currently understood is initiated by an inflammatory phase, which is determined by the invasion of neutrophils and later macrophages, also potentially involving degeneration. The presence of inflammatory cells within the tissue starts immediately after injury and lasts up to several weeks. The regenerative phase follows, which is subsequently followed by fibrosis. The two arrows indicate in a schematic sense the early (immediate) and 1-week delayed application time points for transplanted MSCs.

Figure 2:
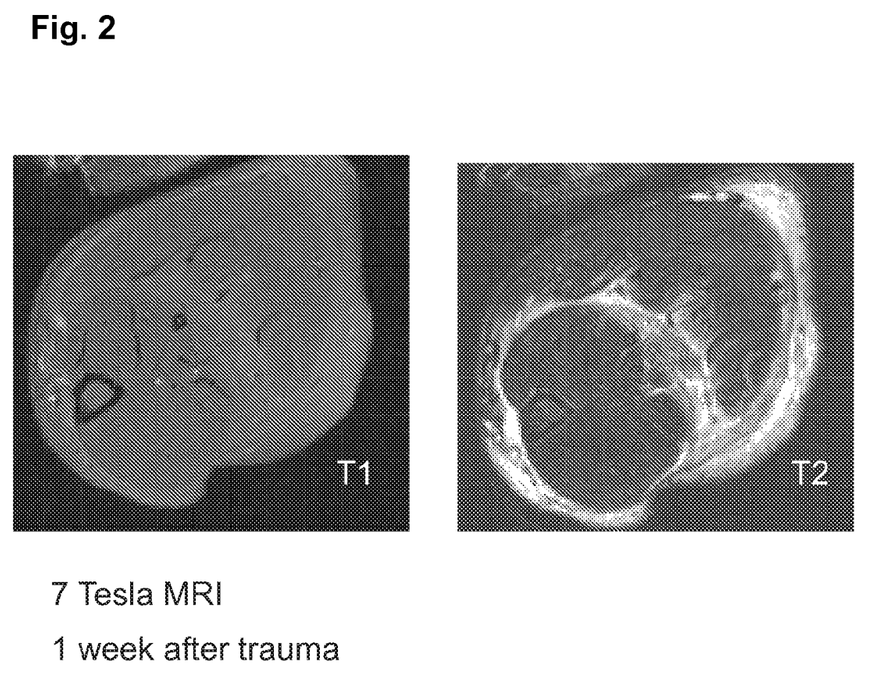
FIGS. 2: T1- and T2-weighted magnetic resonance scans of the left lower extremity of a rat of group 3 one day after crush injury.

FIGS. 2: T1- and T2-weighted magnetic resonance scan of the left lower extremity of a rat of group 3 one day after crush injury to illustrate the selective single muscle trauma. Muscle trauma was carried out as described below in the examples.

Figure 3:
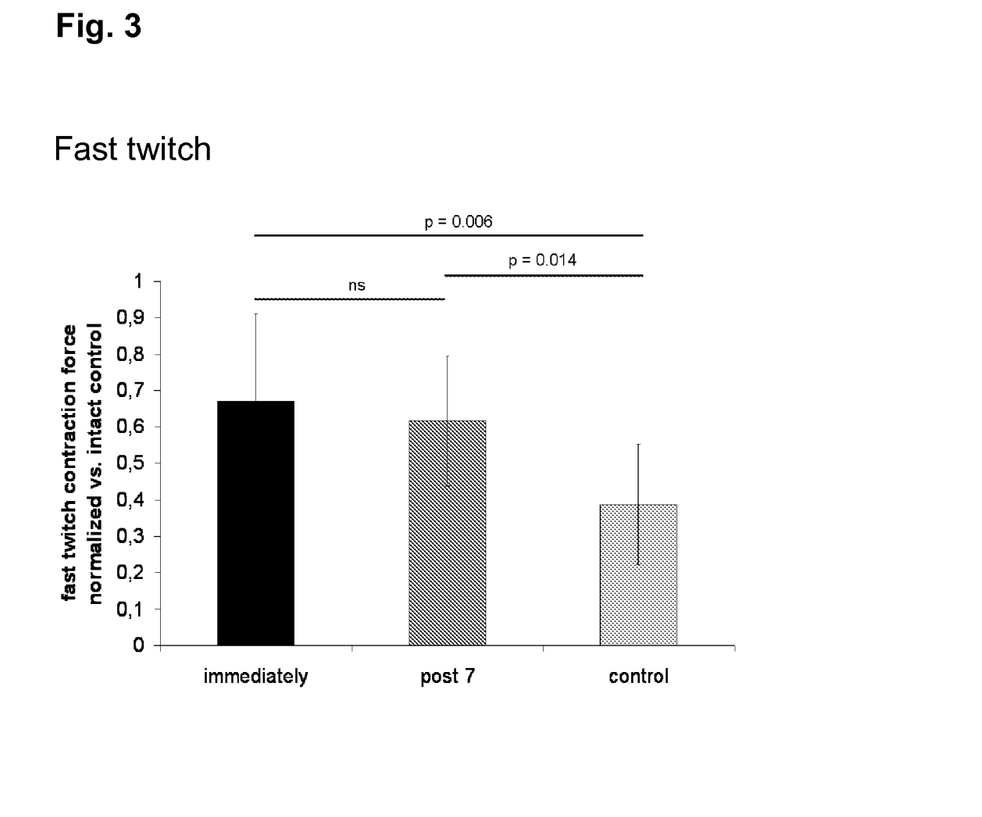
FIG. 3: Functional regeneration of injured muscle as measured by twitch contraction forces using a muscle force measuring device.

FIG. 3: Functional regeneration of injured muscle as measured by twitch contraction forces using a muscle force measuring device. The transplantation of MSCs one week after trauma improved the functional regeneration of the injured muscles as displayed by significantly higher contraction forces in group 2. Local transplantation of the same number of MSCs immediately after crush injury was able to enhance the regeneration process to a similar extent with an increase of maximum twitch contraction forces by 73.3% compared to the control group.

Figure 4:
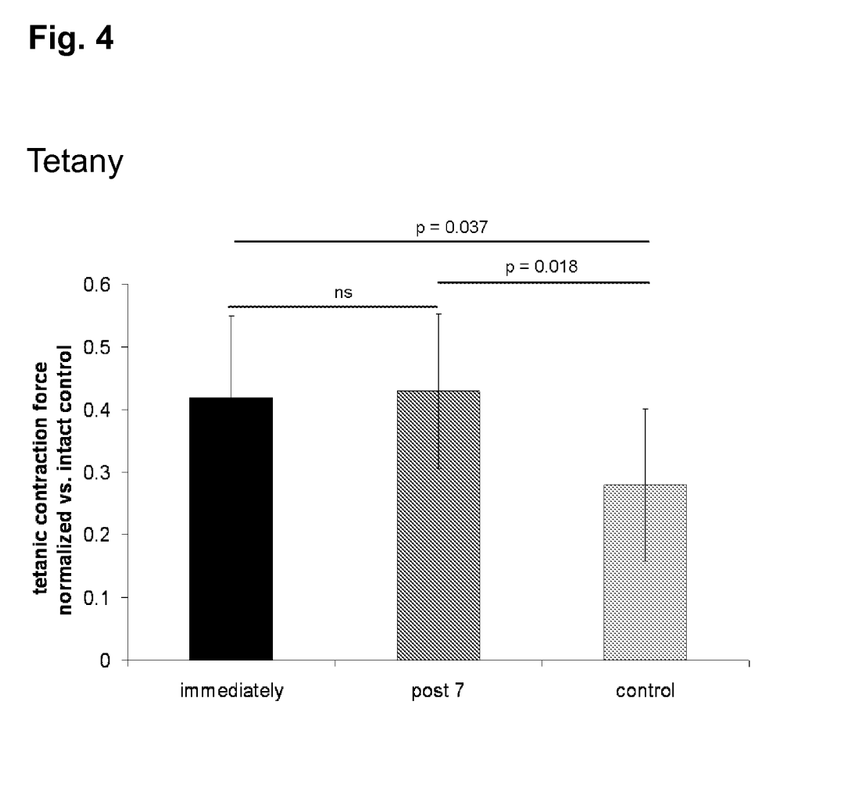
FIG. 4: Functional regeneration of injured muscle as measured by tetanic contraction forces using a muscle force measuring device.

FIG. 4: Functional regeneration of injured muscle as measured by tetanic contraction forces using a muscle force measuring device. The transplantation of MSCs one week after trauma improved the functional regeneration of the injured muscles as displayed by significantly higher contraction forces in group 2. Local transplantation of the same number of MSCs immediately after crush injury was able to enhance the regeneration process to a similar extent with an increase of maximum tetanic contraction forces by 49.6% compared to the control group.

Figure 5:
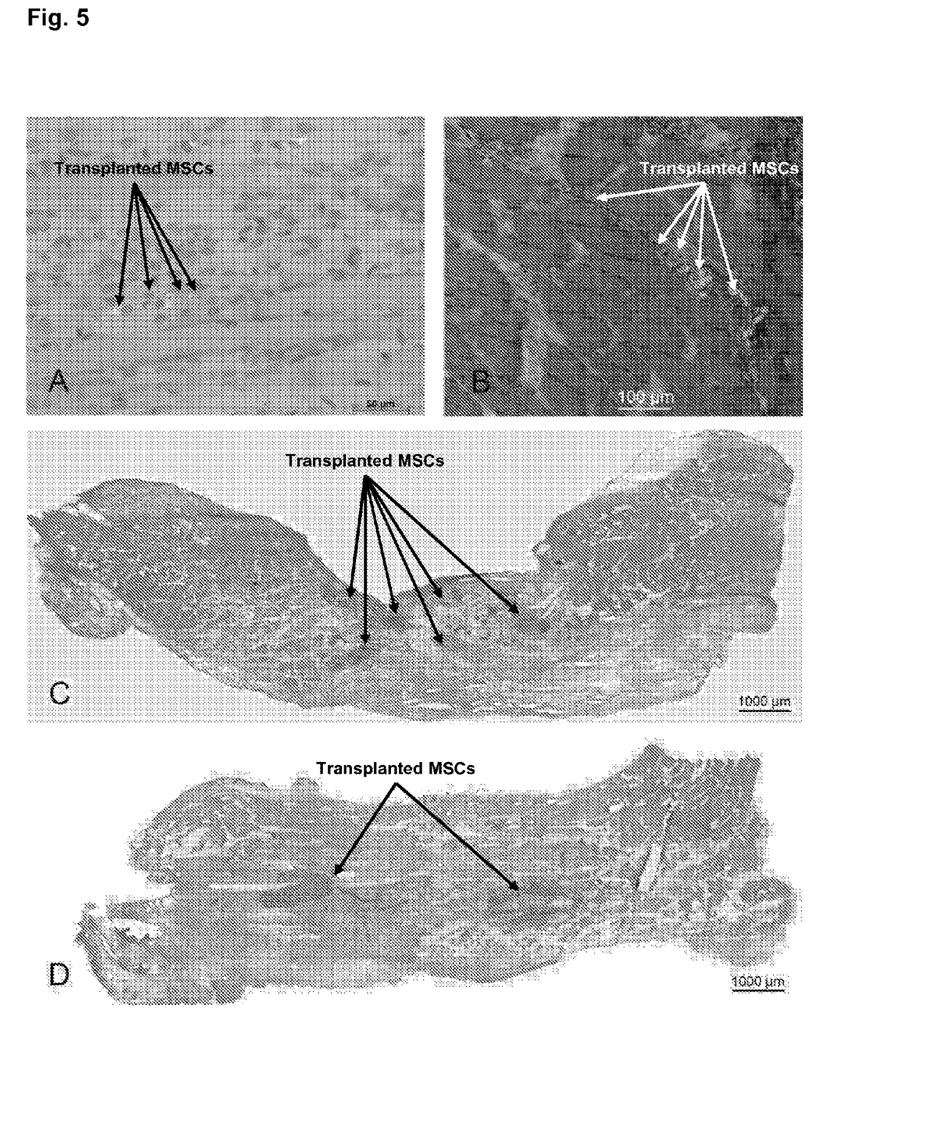
FIG. 5: Tracking of Green Fluorescent Protein (GFP)-labeled MSCs.

FIG. 5: Tracking of Green Fluorescent Protein (GFP)-labeled MSCs. A: Methylene blue section 3 days after immediate transplantation showing MSCs in the interstitial connective tissue between regenerating myofibers. B: Matched H&E section of a muscle treated with transplanted MSCs immediately after trauma and explanted 4 weeks after transplantation showing groups of GFP+ MSCs between mature myofibers. C and D: Representative H&E sections of soleus muscles explanted 3 days after transplantation. The gridded marks and arrows indicate areas where GFP+ MSC pools were found in the muscles. (C: immediate, D: delayed transplantation). In the immediately transplanted muscles the cells were found in smaller groups and distributed over a larger area than in the delayed transplanted muscles, where the cells were found mostly around the needle track.

EXAMPLES

The invention is further described by the following examples. These are not intended to limit the scope of the invention.

The experimental examples relate to treatment of rats with skeletal muscle trauma. The rats represent a mammal model, used to demonstrate the invention by way of example. Other mammals, such as animals and humans, can also be treated by the method of the present invention.

Bone marrow aspirations were taken from both tibiae of each animal and autologous MSC cultures obtained from the material (as described below). Two weeks later, the animals were separated into three groups (each n=9) and the left soleus muscles were bluntly crushed. In group 1 $2 \times 10^6$ MSCs were transplanted into the injured muscle immediately after trauma, whereas group 2 and 3 received an injection of saline. Another week later the left soleus muscles of the animals of group 2 were transplanted with the same number of MSCs. Group 1 and 3 received a sham treatment with the application of saline solution in an identical manner. In vivo functional muscle testing was performed three weeks after transplantation to quantify muscle regeneration.

The following methods were used in carrying out the present invention as demonstrated in the examples. They are intended to further describe the invention by way of practical example and do not represent a limiting description of the invention.

Animals

Sixty female Sprague Dawley rats weighing 140-160 g (Charles River, Sulzbach, Germany) were used in carrying out the examples described below. The animals were housed at a constant temperature of 25° C. with free access to pellet food and water. All animal experiments were carried out according to the policies and principles established by the Animal Welfare Act, the NIH Guide for Care and Use of Laboratory Animals and the national animal welfare guidelines. The study was approved by the local legal representative (State Office for work protection, health protection and technical safety, Berlin: Reg 0290/09).

Bone Marrow Biopsies and Cell Culture

Rats were anesthetized by inhalation of isoflurane (flow 2%) and $N_2O/O_2$. Rimadyl 5 mg/kg body weight was injected subcutaneously before all surgical procedures. The bilateral knees were shaved and disinfected with povidone-iodine. A 5 mm longitudinal incision was made medially of the tibial tubercle. The cortical bone was opened using a 1 mm manually driven drill. Through this window bone marrow was aspirated twice with an 18 gauge canula and stored in 10 ml culture medium (DMEM+10% FCS+penicillin+streptomycin, Sigma, Deisenhofen, Germany). The wounds were closed in one layer.

The cell suspensions were centrifuged (250 g, 10 min), re-suspended in culture medium (DMEM+10% FCS+penicillin+streptomycin, Sigma) and seeded on 75 $cm^2$ culture flasks (Falcon, Heidelberg, Germany). Culture Medium was renewed at two-day intervals. At about 60% confluence of the cellular layer, cells were transferred to 300 $cm^2$ cell culture flasks using 0.25% trypsin (Sigma) and cultivated over two further passages.

MSC Characterization

FACS analysis of surface marker proteins of the cultivated cells showed an expression pattern characteristic for mesenchymal stem cells ($CD44^+$, $CD73^+$, $CD90^+$ and $CD45^-$). The following antibodies were used: mouse ($\alpha$-rat CD44) (Serotec, Duesseldorf, Germany), mouse ($\alpha$-rat CD45) and mouse ($\alpha$-rat CD90) (Acris Antibodies, Hiddenhausen, Germany), mouse ($\alpha$-rat CD73) and rat ($\alpha$-mouse IgG) (BD Biosciences, Heidelberg, Germany). Furthermore routine MSC tests with a cultivation of the cells in osteogenic and adipogenic media demonstrated a full differentiation potential into these lineages. Osteogenic medium (OM) consisted of culture medium supplemented with 200 µM ascorbic acid, 7 mM β-glycerolphosphate and 0.01 µM dexamethasone. Adipogenic medium consisted of culture medium supplemented with 1 µM dexamethasone, 2 µM insulin, 200 µM indomethacine and 500 µM isobutylmethylxanthine.

Skeletal Muscle Trauma

Rats were anesthetized as described above. The left leg was shaved and disinfected. An open crush injury of the soleus muscle was performed as described before. In short the soleus muscle was dissected cranially and caudally to the neurovascular structures and the muscle crushed with a curved artery forceps (Aesculap, Tuttlingen, Germany), which jaws were protected by polyethylene tubes (Braun, Germany) to avoid lesions of the fascia. The forceps was therefore introduced distally directly next to the Achilles tendon and closed for 20 seconds. This procedure was repeated proximally 2 times always in direct continuity to the respective distal crush. The insertion of the neurovascular bundle was spared and 2 crushes performed proximally to this area in the above described manner. FIG. 2 shows a T1- and T2-weighted magnetic resonance scan of the left lower extremity of a rat of group 3 one day after crush injury to illustrate the selective single muscle trauma.

MSC Transplantation and Sham Injections

Cells were detached using 0.25% trypsin, centrifuged, washed twice with phosphate buffered saline (PBS) and re-suspended in 20 µl 0.9% saline solution. $2 \times 10^6$ MSCs were injected into the soleus muscle through a 25 gauge canula either immediately (group 1) or 7 days after trauma (group 2). The animals of group 3 (control group) and group 1 received an injection of 20 µl saline solution into the traumatized muscle 7 days after trauma. For injections the wounds were re-opened distally to safely identify the soleus muscle for transplantation.

Biomechanical Evaluation

The animals were anesthetized with an intraperitoneal injection of ketamine (50/mg/ml) and medetomidine (1 mg/ml) 4:1 weight-adapted after an initial isoflurane narcosis and the sciatic nerve and the soleus muscle were exposed conserving all neurovascular structures. The procedure was first performed on the right leg followed by the left leg after the first measurement. The tendon of the soleus muscle was separated from the Achilles tendon. The lower extremity was fixed into the muscle force measuring device (Experimetria, Budapest, Hungary). The soleus muscle tendon was connected to the force transducer via a suture (4-0, silk) and the muscle was stretched to its reference length, which is the length where maximum twitch tension is elicited by a single supramaximal stimulus, by adjusting the pre-tension of the muscle to 0.15 N. The tension necessary for attaining the reference length of the soleus muscles of the rats was determined in previous experiments. Subsequently the sciatic nerve was stimulated bipolarly in two different modes. In the fast twitch mode 6 pulses at 9 mA/75 Hz with a duration of 0.1 s and 5 s intervals were used. After this the maximum muscle strength was evaluated via sciatic stimulation periods of 3 s at 9 mA/75 Hz for 6 times with 5 s intervals, reaching tetany in all cases.

The animals were sacrificed by an intraperitoneal overdose of anesthetic after quantification of muscle strength. Muscle contraction forces under fast twitch and tetanic stimulation were intraindividually normalized to the uninjured right soleus muscle.

Statistical Analysis

The arithmetic mean and standard deviation were determined for each measurand. Statistical significance analysis was performed using the non-parametric Wilcoxon test for dependent samples when comparing measurands intraindividually. The non-parametric Mann-Whitney-U test for independent samples was used for comparisons between the treatment and the control group. The level of significance was set to 0.05.

GFP Labeling $3 \times 10^6$ HEK293 cells were cultivated overnight in a cell culture plate in 9 ml Dulbecco's Modified Eagle Medium (DMEM, Invitrogen, Carlsbad, USA) with fetal calf serum (FCS, Biochrom AG, Berlin, Germany) until reaching 50-70% confluence. On the next day a mix of 20 µl packaging plasmid and 2 µg cop GFP expression construct (both System Biosciences, Mountain View, USA) was diluted in 400 µl DMEM without FCS and antibiotics. 30 µl Lipofectamine reagent (Invitrogen, Carlsbad, USA) was diluted in 400 µl DMEM without serum, added to the plasmid mix solution and incubated at room temperature for 20 minutes.

The plasmid/lipofectamine reagent construct was added dropwise to the HEK293 cell culture and incubated at 37° C. for 48 hours. The supernatant was collected 48 hours post-transfection and filtered with a 0.45 µm filter. The produced pseudovirus was used for transduction or stored at −80° C.

$1.5 \times 10^6$ target MSCs were seeded in a T175 cell culture flask and cultured overnight. The target MSCs were infected by adding 5 ml of the pseudovirus, 10 ml DMEM with FCS and 15 µl protamin sulfate and incubated at 37° C. with 5% $CO_2$. After 24 hours media change with DMEM with serum and antibiotics (penicilline, streptomycin, Sigma, Taufkirchen, Germany) followed. The infected target cells were further cultivated and analyzed at day 6 post transduction for expression using FACS and fluorescence microscope. Transduction efficiency reached at least 85% in all cases. At day 7 post transduction the MSCs were washed with PBS, detached with 2.5 ml trypsin, harvested in DMEM, centrifuged and transplantated in 20 µl of saline.

Histologic Analysis

The rats were anesthetized by an intraperitoneal injection as described above and the soleus muscles were explanted. The animals were sacrificed by an intraperitoneal overdose of anesthetic. Muscles explanted 4 weeks after trauma were fixated in 4% paraformaldehyde, dehydrated, embedded in paraffin and sectioned longitudinally (4 µm).

For connective tissue evaluation, deparaffinized and rehydrated sections were incubated for 60 minutes in sirius red solution. Therefore 5 g sirius red were dissolved in 500 ml saturated picric acid (Fluka/Riedel de Häen, Seelze, Germany). Differentiation was reached by two washes with diluted acetic acid. Finally, a short dehydration in graded alcohols was made.

A blinded investigator evaluated the amount of collagenous connective tissue in the muscles. In order to measure the total area of endo- and perimysial fibrosis, images of whole longitudinal sections of the muscle were collected from the distal to the proximal tendon by using a Leica DMRB light microscope (Leica, Wetzlar, Germany) and digital camera (AxioCam MRc, Carl Zeiss, Göttingen, Germany). Images were correlated and connected to obtain the whole longitudinal sections with the help of the Axio Vision program (Rel. 4.4, Carl Zeiss, Göttingen, Germany). These compound pictures were then edited with an image analysis system (KS 400 3.0, Carl Zeiss, Göttingen, Germany).

Tendinous structures were removed by the investigator and the absolute area of red connective tissue was measured and normalized to the total muscle area. For analysis of vessel density an immunohistochemical stain against alpha-Smooth Muscle Actin (SMA) was used. Arterial and venous vessels with a diameter beneath and above 40 µm were counted. H & E staining was used for descriptive analysis of the trauma. Muscles explanted on day 3 after GFP+-MSC transplantation were immediately frozen in 2-methyl butane cooled in liquid nitrogen and stored at −80° C. until further processing. 6 µm longitudinal sections were obtained from the specimens and stained with H&E or DAPI, serving as a nuclear counterstain.

Example 1

Results of In Vivo Functional Muscle Testing

Fast twitch stimulation of the healthy right soleus muscles of all animals resulted in an average contraction force of 0.52±0.14 N. No decrease of successive contraction peaks was observed in uninjured or injured muscles irrespective of treatment. Stimulation with 9 mA and a frequency of 75 Hz at a duration of 3 seconds yielded tetanic contractions in all tested muscles reflecting their maximum contraction capacity. The latter amounted to 0.98±0.27 N in the uninjured soleus muscles. Tetanic maxima showed a continuous, linear decrease with successive stimulations in all muscles. This decrease could be described by a decline gradient, which was significantly different between the traumatized left and the non-traumatized right soleus muscles [−0.015±0.009 (left) vs. 0.031±0.014 (right), p-value<0.001]. The decline of the tetanic contractions was not influenced by cell therapy.

The ratio of fast twitch and tetanic forces represents the contraction reserve of a muscle exceeding a single twitch. 4 weeks after trauma this ratio showed a significant difference between traumatized and healthy muscles with a mean value of 0.80±0.12 (left) and 0.54±0.15 (right), p<0.001). No difference could be observed between the twitch/tetanus ratios of the treatment and the control groups.

Maximum contraction forces after twitch stimulation were reduced to 39±18% of the non injured right control side after crush trauma of the soleus muscles as measured in group 3. Tetanic stimulation revealed a reduction of the maximum contraction capacity of 72±12% of the value obtained from intact internal control muscles. The transplantation of $2 \times 10^6$ MSCs one week after trauma improved the functional regeneration of the injured muscles as displayed by significantly higher contraction forces in group 2 (twitch: p=0.014, tetany: p=0.018), as shown in FIGS. 3 and 4. Local transplantation of the same number of MSCs immediately after crush injury was able to enhance the regeneration process to a similar extent with an increase of maximum twitch contraction forces by 73.3% (p=0.006) and of maximum tetanic contraction forces by 49.6% (p=0.037) compared to the control group. A comparison of the contraction forces between muscles treated by immediate and by delayed transplantation showed no significant difference between groups with p-values of 0.93 (fast twitch) and 0.73 (tetany).

The twitch/tetanus ratios, which describe the reserve contraction capacity of a muscle, were not altered by MSC therapy when compared to the control. Whereas a healthy rat soleus muscle is able to almost double its contraction force when stimulated with repetitive pulses in tetanic mode, injured muscles only show a reserve of 25% of their twitch force. In view of the significantly and equally higher forces in the therapy groups under both stimulation modes twitch and tetanic, it can be assumed that MSC transplantation resulted in an increase in contractile muscle substance rather than in a modulation of electrophysiological processes, as facilitation of muscle force development.

Example 2

Results of Histological Analysis

H&E stains of muscles harvested 3 days after injury still showed a pronounced inflammatory reaction throughout the soleus with the infiltration of predominantly macrophages, but also of neutrophils and lymphocytes. Most of the necrotic myofibers had already been removed and multiple groups of regenerating centronucleated fibers could be observed surrounded by loose connective tissue with the above described inflammatory infiltration. In muscles harvested 10 days after crush injury the inflammatory reaction had almost disappeared. The connective tissue showed a condensation towards a more dense type, although still with active fibroblastic nuclei.

Three days after both immediate and delayed transplantation, groups of GFP+ MSCs or single MSCs could be observed in the cryosectioned soleus muscles. Representative pictures can be seen in FIGS. 5A and B. The transplanted MSCs were found predominantly in the interstitium throughout the muscles, a few cells also in connective tissue underneath the muscle fascia. As expected, the distribution profile of GFP+-MSCs in the muscles of the two treatment groups differed to a certain extent, with more discriminable groups of MSCs in animals transplanted immediately after injury compared to animals transplanted 7 days after trauma and with a larger area covered by the MSCs in the sections (FIGS. 5C and D). MSCs were also found in proximity to blood vessels, nerves and myofibers.

In both treatment groups, immediate and delayed transplantation, GFP+-MSCs could also be detected in muscles explanted four weeks after trauma, although to a lesser extent. Interestingly, in the muscles after delayed transplantation only very few GFP+-MSCs could be detected, whereas in the immediately transplanted muscles they could still be found as small groups in one or two circumscribed areas of the muscle. The GFP+-MSCs were not found within scar tissue but between regenerated muscle fibers in the interstitial compartment.

No significant difference could be observed between the treatment groups and the control group in regards to the extent of collagenous fibrotic tissue in the muscles 4 weeks after injury. The number of blood vessels with diameters above and beneath 40 μm 4 weeks was also measured. As is typical for this injury pattern, the number of small vessels rose significantly in all injured muscles. The number of blood vessels with diameters above 40 μm stayed constant. A significant reduction of small blood vessels compared to injured control muscles could be observed after immediate transplantation (21.4 vessels/mm² (control) vs. 18.5 vessels/mm² (immediate), p-value=0.045). Given the basis of 11.1 small vessels per mm² in the uninjured soleus this represents a reduction of 21% of the additional small vessels after injury.

In the presented injury model the blood supply to the muscle has been preserved in order to avoid severely ischemic conditions within the muscle. Of course, also due to the injury of intramuscular blood vessels, posttraumatic vasculogenesis took place, reflected by an increase in small sized vessels, but obviously the transplanted cells did not receive a hypoxic trigger for the secretion of angiogenic factors. On the contrary, the data show that—at least after immediate transplantation—less blood supply was necessary to achieve the improvement in contraction forces.

The invention claimed is:

1. A method of treating a skeletal muscle injury in a human subject in need thereof, comprising administering to the subject a therapeutically effective amount of autologous or allogeneic mesenchymal stem cells (MSCs), wherein the MSCs are positive for CD44, CD73, and CD90, and negative for CD45, CD34, CD14, CD11b, CD19, CD79a, and HLA-DR;
    wherein the skeletal muscle injury is an injury incurred during hip replacement, an injury incurred during surgery of the spine, an injury incurred by cutting or dissection of or surgical incision into skeletal muscle, an injury incurred during operative or surgical intervention, an injury incurred during myotomy, an injury incurred from surgery or operation around the spinal cord, or an injury incurred from surgery or operation around the vertebral column;
    wherein said administration occurs within less than 24 hours after the muscle injury;
    wherein the therapeutically effective amount of MSCs administered is between $1 \times 10^4$ and $1 \times 10^{10}$ MSCs/kg body weight; and
    wherein the treatment enhances the functional recovery of the skeletal muscle, or regenerates structure of the skeletal muscle, or reduces pain associated with the skeletal muscle injury.

2. The method of claim 1, wherein the MSCs are bone marrow MSCs.

3. The method of claim 1, wherein the autologous MSCs are obtained from the patient interoperatively during the same operation in which the MSCs are administered.

4. The method of claim 2, wherein the bone marrow MSCs are concentrated by depletion of red blood cells from a bone marrow aspiration, and prepared from the bone marrow as a nuclear cell fraction.

5. The method of claim 1, wherein the MSCs are obtained from a patient before elective surgery.

6. The method of claim 1, further comprising expanding the MSCs by cell culture in vitro.

7. The method of claim 1, wherein the skeletal muscle injury is an injury incurred during hip replacement.

8. A method of treating a skeletal muscle injury in a human subject in need thereof, comprising administering to the subject a therapeutically effective amount of autologous or allogeneic mesenchymal stem cells (MSCs), wherein the MSCs are positive for CD44, CD73, and CD90, and negative for CD45, CD34, CD14, CD11b, CD19, CD79a, and HLA-DR;
    wherein the skeletal muscle injury is selected from sport injuries, torn muscles, torn muscle fibers, injuries incurred from stretching muscles, injuries incurred from overstretching muscles, traumatic soft tissue injury with concomitant skeletal muscle injury, or injuries incurred in association with a rotator cuff injury or a rotator cuff rupture;

wherein said administration occurs within less than 24 hours after the muscle injury;

wherein the therapeutically effective amount of MSCs administered is between $1\times10^4$ and $1\times10^{10}$ MSCs/kg body weight; and wherein the treatment enhances the functional recovery of the skeletal muscle, or regenerates structure of the skeletal muscle, or reduces pain associated with the skeletal muscle injury.

9. The method of claim 1, wherein the MSCs are administered locally to injured muscle or to healthy tissue surrounding the injured muscle.

10. The method of claim 9, wherein the MSCs are administered within 0.5 mm to 100 mm of the muscle injury, 0.5 mm to 50 mm of the muscle injury, or 0.5 mm to 50 mm of the muscle injury.

11. The method of claim 1, wherein the MSCs are administered via injection.

12. The method of claim 1, wherein the MSCs are administered via an arterial blood vessel leading to the site of muscle injury.

13. The method of claim 1, wherein the MSCs are administered in a pharmaceutical composition comprising a therapeutically effective amount of MSCs and a pharmaceutically acceptable substance.

14. The method of claim 1, wherein the MSCs are genetically modified.

15. The method of claim 14, wherein the MSCs are genetically modified to produce and secrete proteins that influence regeneration or inflammatory processes.

16. The method of claim 1, wherein the MSCs are linked or coupled to proteins or other substances in vitro in order to influence the regeneration or inflammatory processes.

17. The method of claim 1, wherein said administration occurs within 18 hours after the muscle injury.

18. The method of claim 1, wherein said administration occurs within 12 hours after the muscle injury.

19. The method of claim 1, wherein said administration occurs within 6 hours after the muscle injury.

20. The method of claim 1, wherein said administration occurs within 1 hour after the muscle injury.

21. The method of claim 1, wherein the skeletal muscle injury is a muscle injury incurred during operative or surgical intervention.

22. The method of claim 18, wherein the skeletal muscle injury is a muscle injury incurred during operative or surgical intervention.

23. The method of claim 20, wherein the skeletal muscle injury is a muscle injury incurred during operative or surgical intervention.

24. The method of claim 8, wherein said administration occurs within 18 hours after the muscle injury.

25. The method of claim 8, wherein said administration occurs within 12 hours after the muscle injury.

26. The method of claim 8, wherein said administration occurs within 6 hours after the muscle injury.

27. The method of claim 8, wherein said administration occurs within 1 hour after the muscle injury.

28. The method of claim 8, wherein the skeletal muscle injury is an injury incurred in association with a rotator cuff injury or a rotator cuff rupture.

* * * * *